(12) United States Patent
Lundgren et al.

(10) Patent No.: US 9,733,190 B2
(45) Date of Patent: Aug. 15, 2017

(54) DEVICE AND METHOD FOR DETERMINING PROCESSING CAPACITY

(75) Inventors: Clas Erik Gunnar Lundgren, Snyder, NY (US); Ronald M. Okupski, East Aurora, NY (US)

(73) Assignee: The Research Foundation for The State University of New York, Buffalo, NY (US)

( * ) Notice: Subject to any disclaimer, the term of this patent is extended or adjusted under 35 U.S.C. 154(b) by 491 days.

(21) Appl. No.: 14/009,694

(22) PCT Filed: Apr. 6, 2012

(86) PCT No.: PCT/US2012/032557
§ 371 (c)(1),
(2), (4) Date: May 19, 2014

(87) PCT Pub. No.: WO2012/139023
PCT Pub. Date: Oct. 11, 2012

(65) Prior Publication Data
US 2014/0242708 A1 Aug. 28, 2014

Related U.S. Application Data

(60) Provisional application No. 61/472,229, filed on Apr. 6, 2011.

(51) Int. Cl.
*G01N 21/78* (2006.01)
*B01D 53/04* (2006.01)
(Continued)

(52) U.S. Cl.
CPC ............. *G01N 21/78* (2013.01); *A62B 27/00* (2013.01); *B01D 53/0454* (2013.01); *B01D 53/62* (2013.01); *A61M 16/22* (2013.01); *A61M 2205/18* (2013.01); *A61M 2205/276* (2013.01); *A61M 2205/3306* (2013.01);
(Continued)

(58) Field of Classification Search
CPC ..................................................... G01N 21/78
See application file for complete search history.

(56) References Cited

U.S. PATENT DOCUMENTS 6,990,980 B2    1/2006  Richey, II
2003/0074154 A1  4/2003  Warkander
(Continued)

*Primary Examiner* — Krishnan S Menon
*Assistant Examiner* — Dwan A Gerido
(74) *Attorney, Agent, or Firm* — Hodgson Russ LLP

(57) ABSTRACT

A system and method for determining a remaining processing capacity of a scrubber having a flow path and a processing material disposed along the flow path. A device may comprise a plurality of optical sensors disposed within the processing material and arranged along the flow path, a light source, and a processor for determining the capacity according to signals received from the optical sensor. The device may be used to illuminate processing material adjacent to each optical sensor using the light source, measure a light value reflected by the processing material at each optical sensor, and determine the remaining processing capacity of the scrubber, using the processor, based on the measured light value. Devices may comprise a memory, such as a non-volatile memory to allow multiple uses of a scrubber without reloading with fresh processing material.

10 Claims, 10 Drawing Sheets

(51) Int. Cl.
*B01D 53/62* (2006.01)
*A62B 27/00* (2006.01)
*A61M 16/22* (2006.01)
*B63C 11/24* (2006.01)

(52) U.S. Cl.
CPC ..... *A61M 2205/50* (2013.01); *A61M 2205/52* (2013.01); *A61M 2205/583* (2013.01); *A61M 2205/8206* (2013.01); *A61M 2209/02* (2013.01); *B01D 2251/302* (2013.01); *B01D 2251/304* (2013.01); *B01D 2251/306* (2013.01); *B01D 2251/404* (2013.01); *B01D 2251/602* (2013.01); *B01D 2251/604* (2013.01); *B01D 2253/102* (2013.01); *B01D 2253/112* (2013.01); *B01D 2253/1124* (2013.01); *B01D 2255/1021* (2013.01); *B01D 2255/1025* (2013.01); *B01D 2257/504* (2013.01); *B01D 2259/40084* (2013.01); *B01D 2259/4533* (2013.01); *B01D 2259/4541* (2013.01); *B63C 11/24* (2013.01); *Y02C 10/04* (2013.01); *Y02C 10/08* (2013.01)

(56) References Cited

U.S. PATENT DOCUMENTS

| | | | |
|---|---|---|---|
| 2006/0201508 A1* | 9/2006 | Forsyth | A62B 7/08 128/204.26 |
| 2008/0077034 A1* | 3/2008 | Baker | A61B 5/0836 600/532 |
| 2010/0012124 A1 | 1/2010 | Roger | |
| 2010/0273209 A1 | 10/2010 | Gideon et al. | |
| 2012/0309101 A1* | 12/2012 | Horn | G01N 21/8507 436/164 |

* cited by examiner

DEVICE AND METHOD FOR DETERMINING PROCESSING CAPACITY

CROSS-REFERENCE TO RELATED APPLICATION

This application claims the benefit of priority to U.S. provisional patent application Ser. No. 61/472,229, filed on Apr. 6, 2011.

FIELD OF THE INVENTION

The present invention relates to a device and method for determining the processing capacity of a processing material, for example, the absorptive capacity of soda lime in a $CO_2$ scrubber used in a re-breather.

BACKGROUND OF THE INVENTION

Processing materials are used in a variety of industries to perform chemical reactions over a period of time. These processing materials have an inherent limit to their reactivity before the materials become depleted. Accurately monitoring the processing capacity of a processing material has proven difficult in the prior art.

One example of how a processing material is used can be found in closed circuit breathing equipment. This equipment, also known as a re-breather apparatus, is frequently used by military and advanced civilian divers, firefighters, and other users who must operate in noxious environments. The advantages of this type of equipment are: (1) superior use time for a given bulk/weight; (2) quiet operation; and (3) bubbles are not released when a user is breathing with the unit in an underwater application.

As the name implies, a user (for example, a diver) breathes in and out on an apparatus in which his/her exhaled gas containing $CO_2$, unused oxygen, and sometimes a diluent gas such as nitrogen, helium, or certain mixtures of inert gases is processed to be available for the next inhalation. The exhaled $CO_2$, which was formed in the diver's body, is retained by a so-called $CO_2$ scrubber, and used oxygen is automatically replaced from a compressed-gas container (or containers) of "make up gas."

The $CO_2$ is removed by being bound chemically to an absorbent material which can be contained in a scrubber canister. The diver's breathing action moves the exhaled gas through the scrubber and into a rubber or plastic bag. This is often called the re-breathing bag. The absorbent typically comprises a mixture of calcium d-hydroxide and sodium hydroxide fashioned into small pellets, or small gravel-like granules. Once the $CO_2$ has been removed, and make-up oxygen (to replace the oxygen used up in the previous breaths) has been added, the gas in the re-breathing bag is available for the diver's next inhalation. The advantage of this system compared to conventional open-circuit scuba gear is that in the re-breather essentially all the oxygen stored in the compressed gas containers is available for the diver's metabolism while in conventional open-system scuba gear, each expiration, including its content of unused oxygen, is exhaled to the surrounding water.

However, re-breathing gear poses challenges, some of which are: (a) economic and logistic; and (b) tactical and safety related. These challenges are overcome by the presently described technology.

In the prior art, it was not possible to reliably predict how much $CO_2$ absorbing capacity is still available in a scrubber after a dive is completed. This is true regardless of whether the soda lime used is of a color-changing indicator type or non-indicator type. Thus, the user must empty the soda-lime canister and put in a fresh charge of soda-lime before each dive. This is cumbersome and expensive. Note that, after partial use, the indicator soda lime typically returns relatively quickly from its violet or other dark color back to white—termed "blanching." This is because the $CO_2$ which is bound to the superficial layers of the absorbent granules, causes a change to violet or other dark color before the $CO_2$ binding action of the deeper layers has had time to take place. During non-use periods of the canister, a redistribution of $CO_2$ occurs within the granules which reduces the amount of $CO_2$ bound to the superficial layers. Thus the indicating dye returns to the white color despite the fact that the total absorbing capacity of the granule has been reduced. It is not possible, by visual inspection, before the start of a dive, to determine how much absorbing capacity remains in the absorbent bed.

A user should be able to plan ahead with regard to the potentially available processing material. This is especially true for a diver attempting to plan ahead with regard to the duration of a dive, whether his/her $CO_2$ scrubber canister has just been charged with fresh absorbent or contains absorbent that has been partially used in previous dives. If the $CO_2$ scrubber's unused absorption time is known at any point in time of usage, this information enables the diver to determine whether enough underwater time is available to return to base after a mission. Furthermore, it would allow a diver to plan for a slow enough ascent time to avoid decompression sickness.

Although this problem is described with reference to a re-breather system, the concept of monitoring the processing capacity of a processing material is not limited to this field. There are many other examples where an accurate method of determining processing capacity would be advantageous.

SUMMARY OF THE INVENTION

The invention provides a device and method for determining processing capacity that is particularly suited for use in a closed-circuit re-breather system, but also is useful in a variety of other fields. For example, the present invention may inform a diver about the potentially safe underwater time that is currently available from start to finish of the dive.

The invention may be embodied as a method for determining a remaining processing capacity of a scrubber. The scrubber has a flow path and a processing material disposed along at least a portion of the flow path. The processing material may be configured to vary in color according to the remaining capacity of the processing material.

The method comprises the steps of providing a device, illuminating the processing material, measuring a light value, and determining the remaining processing capacity of the scrubber, using the processor, based on the measured light value.

The provided device comprises one or more of optical sensors disposed within the processing material and arranged along the flow path of the scrubber, a light source configured to illuminate the processing material adjacent to the optical sensors, and a processor. In some embodiments, the device has a memory, and the method further comprises the step of storing the measured light value from each optical sensor in the memory. The memory may be non-volatile such that stored information is not lost if the memory loses power. In another embodiment, the method further comprises the step of storing the determined remaining processing capacity in the memory.

The illuminating step involves directing light energy toward the processing material adjacent to each optical sensor using the light source.

The optical sensor measures a light value reflected by the processing material at each optical sensor. The measured light value may be the luminance of the reflected light, the wavelength of the reflected light, or some other optical characteristic of the reflected light.

In some embodiments, the remaining processing capacity of the scrubber is determined based on the measured light value over time.

In another embodiment, the steps of illuminating the processing material, measuring the light value at each optical sensor, and storing the measured light values, are repeated at least once, and the remaining processing capacity is determined using the rate of change of the measured light values.

In some embodiments, the method further comprises the step of displaying the remaining processing capacity on a display.

The invention can also be described as a device for determining a remaining processing capacity of a scrubber. The scrubber has a flow path and contains a processing material disposed along at least a portion of the flow path, the processing material configured to vary in color according to the remaining capacity of the processing material.

The device comprises one or more optical sensors, a light source, and a processor. The optical sensors are for measuring reflected light values from the processing material. The optical sensors may be configured to be disposed proximate the processing material and arranged along at least a portion of the flow path.

The device comprises a light source configured to illuminate the processing material proximate the plurality of optical sensors. In some embodiments, the light source comprises a plurality of light sources, and each light source of the plurality of light sources corresponds to an optical sensor of the plurality of optical sensors.

The processor may be in communication with the optical sensors and the light source. The processor may be programmed to determine a remaining processing capacity of the scrubber based on the light values reflected by the processing material measured by each optical sensor. The processor may also be programmed to determine an estimated remaining time based on the remaining processing capacity and the rate of change of the processing capacity. In another embodiment, the processor may be programmed to determine a rate of processing capacity consumption.

In some embodiments, the device further comprises a memory in electrical communication with the processor. The memory may be configured to store the reflected light values. In another embodiment, the memory is non-volatile.

In some embodiments, a final light source and a final optical sensor are located near an exit of the scrubber with respect to the flow path.

In some embodiments, the device further comprises a display in communication with the processor for displaying a determined remaining processing capacity.

The invention disclosed herein may be embodied as a low cost, self-contained, battery operated device and related software which, when placed in a $CO_2$ scrubbing canister, will significantly enhance the safety of diving with rebreather-type self-contained underwater breathing apparatus. It can digitally display in the diver's facemask, or in some similar fashion, so as to be readable by the diver how much longer, in hours and minutes (with a safety margin) he/she can stay submerged without risking $CO_2$ poisoning. Normally this number will continue to decrease as the soda lime is used up. If, however, the diver decreases his/her work effort, thus slowing the production of $CO_2$, the available time will increase compared to the prognosticated time during the earlier phase of the dive when the diver was more active.

This disclosure pertains to a device and method that will make the use of closed-circuit rebreathing gear for divers, firefighters, etc., safer, more practical and economic. Typically, such breathing gear contains a $CO_2$ scrubber which removes $CO_2$ from the diver's exhaled gas. This scrubbed gas is then available for the next inhalation after the oxygen that was missing in the exhaled gas has been replenished. The device and method according to the present invention may comprise an electronic circuit which monitors how much $CO_2$ absorbent capacity, referred to as $CO_2$ absorption time, is unused at any point of time during a dive. Thus, the invention prognosticates and informs a diver how much time remains during which he/she can safely remain submerged. The circuitry used herein may include a microcontroller which collects data from an plurality of optical sensors which, when illuminated by a white LED, monitor the color change (typically from white to violet in an "indicator soda lime") or, in another embodiment, the change in intensity of reflected light that normally occurs as the soda lime is depleted and its color or light reflection changes as the white color of the unused soda lime changes to a darker color. Based upon the rate of advancement of the color change from white to violet (or other darker-than-white color), along the path of gas flow, and the fact that the microcontroller knows the $CO_2$ absorption time available at the start of a dive, the availability of unused $CO_2$ absorption time can be predicted. This availability is calculated, based on the used-up time and diver activity level. In other words, the rate of $CO_2$ production of the diver determines the remaining $CO_2$ absorption time, i.e., dive time.

BRIEF DESCRIPTION OF THE DRAWINGS

For a fuller understanding of the nature and objects of the invention, reference should be made to the accompanying drawings and the subsequent description. Briefly, the drawings are.

FURTHER DESCRIPTION OF THE INVENTION

Figure 1A:
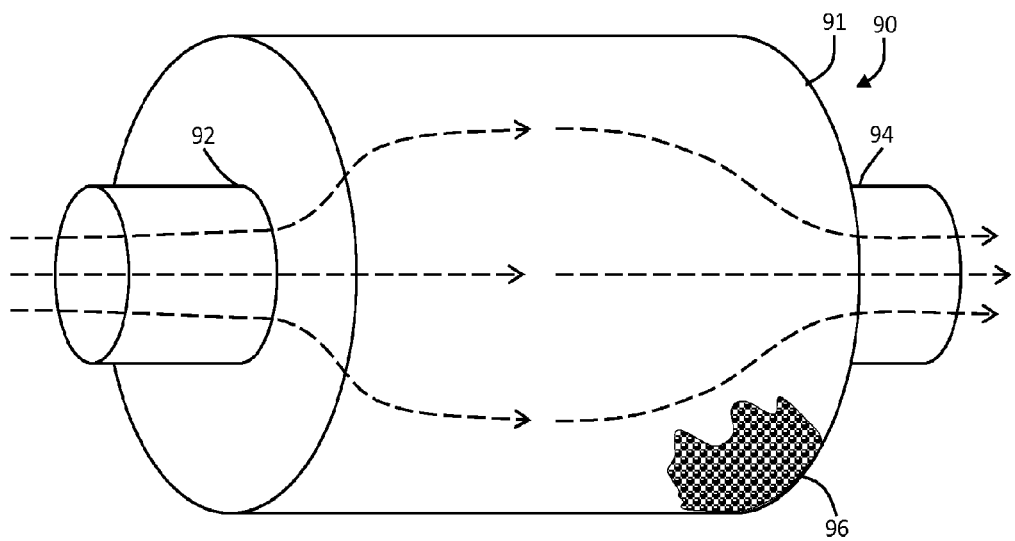
FIG. 1A depicts an exemplary prior art scrubber where only a portion of the processing material is shown.

The present invention may be embodied as a device 80 for use with a scrubber 90 to determine a remaining processing capacity of the scrubber 90. As used herein, "scrubber" refers generally to an apparatus for processing a substance, the scrubber 90 comprising a vessel 91 having a flow path by which an inlet 92 of the vessel 91 communicates with an outlet 94 of the vessel 91 (see, e.g., FIG. 1A—wherein the flow path is generally represented by dashed arrows). The vessel 91 contains a processing material 96 disposed along at least a portion of the flow path. As such, the substance to be processed is moved through the processing material 96 along the flow path. Specific reference is made herein to exemplary scrubbers 90 for removing carbon dioxide from a gas mixture—for example, a scrubber 90 suitable for use in a closed-circuit breathing apparatus—however, it should be recognized that the term scrubber 90 should be interpreted broadly as an apparatus for processing a substance.

Processing capacity refers to the amount of substance the processing material of a scrubber is able to process. Generally, the processing capacity of scrubbers may vary based on the type of processing material used, the amount of processing material used, environmental factors, and other details of the reaction processes. Processing capacity may be represented in terms of volume, time, color, and/or any other characteristic, and these representations may be a measure of spent capacity, remaining capacity, or both.

Figure 1B:
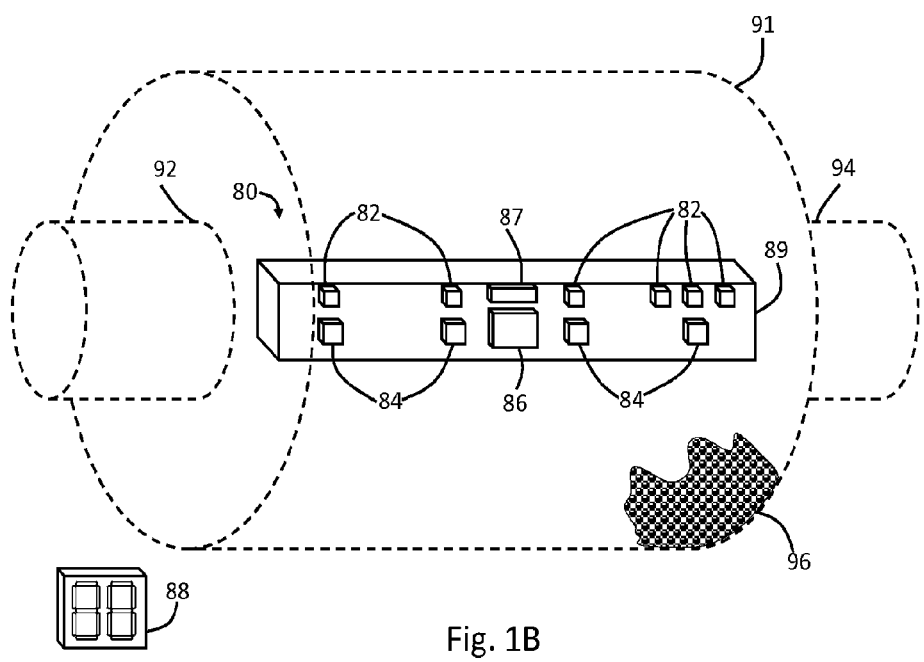
FIG. 1B depicts a device according to an embodiment of the present invention and disposed in a scrubber (shown with dashed lines). Only a portion of the processing material is shown.

The device 80 comprises one or more optical sensors 82 configured to measure an optical characteristic of the processing material 96 (see, e.g., FIG. 1B). The optical characteristic may be, for example, a reflected light value, a wavelength of received light (color), a phase change of received light, an intensity of received light, etc. The optical sensor(s) 82 may be a CMOS sensor, CCD sensor, or other optical sensors known in the art. The optical sensor(s) 82 convert the measured optical characteristic into an electronic signal(s) representing the measurement.

The optical sensor(s) 82 are configured to be disposed in at least a portion of the flow path. Where multiple optical sensors 82 are used, the optical sensors 82 are arranged such that the optical sensors 82 are disposed along the flow path when the device 80 is used with a scrubber 90. In such embodiments with multiple optical sensors 82, the optical sensors 82 may or may not be evenly spaced along the flow path. For example, optical sensors 82 may be configured to be grouped near the inlet 92 and/or the outlet 94 of a scrubber 90, optical sensors 82 may be used in multiples (e.g., doubled for redundancy) at points along the flow path, etc.

The device 80 further comprises a light source 84. The light source 84 may be configured to emit light over a broad range of wavelengths, or be configured to emit light of a specific wavelength (or a narrow range of wavelengths). For example, the light source 84 may emit white light (broad range) or infrared light (narrow range). The light source 84 may be a light-emitting diode ("LED"), a light emitting bar, a filament, or other device capable of emitting light. When activated, the light source 84 may illuminate the processing material 96 proximate the plurality of optical sensors 82, the substance, or both.

A single light source 84 may cooperate with one or more optical sensors 82. In other embodiments, the light source 84 may further comprise more than one light source 84. In such embodiments, each light source 84 may relate to one or more optical sensors 82. For example, each light source 84 may cooperate with one optical sensor 82, more than one light source 84 may cooperate with an optical sensor 82, or any other ratio of light sources 84 to optical sensors 82.

The device 80 further comprises a processor 86. The processor 86 may be a microcontroller, field-programmable gate array ("FPGA"), or any other suitable processor. The processor 86 is in communication with the one or more optical sensors 82 and the light source 84. For example, the processor 86 may be mounted to a printed circuit board along with a plurality of optical sensors 82 and light sources 84. In this example, the processor 86 is in communication with the optical sensors 82 and light sources 84 through an electrical conductor, such as a trace or wire. The optical sensors 82 and light sources 84 may communicate with the processor 86 wirelessly, for example, through the use of a wireless receiver and transmitter.

The processor 86 is programmed to determine a remaining processing capacity of a scrubber 90 based on electrical signals (previously described) received from the optical sensor(s) 82. It should be noted that remaining capacity is related to the depleted (or used) capacity, and the present invention is equally suited to either model of capacity determination. Such capacity determination may be made directly from the values measured by the optical sensors 82 and/or algorithmically based on such information as the measurements at each sensor, historical information, etc.

The processor 86 may be programmed to determine an estimated remaining time before processing material exhaustion based on the remaining processing capacity and the rate of change of the processing capacity. Because the optical sensors 82 are placed along the flow path of a scrubber 90, the processor 86 can detect how quickly the processing material is being depleted. For example, if five optical sensors 82 are placed in the flow path, the processor 86 can determine a processing capacity percentage based on which optical sensors 82 indicate depletion (e.g., if the first three optical sensors 82 of the five indicates depletion, the processor 86 may estimate 40% of the processing capacity remains).

The device 80 may comprise a memory 87 in communication with the processor 86 for storing data. The processor 86 may use such stored data to more accurately determine a remaining processing capacity. The memory 87 may store, for example, previous measurements of the optical sensors 82, previous determined remaining capacities, instructions, etc. As such, the processor 86 may use historical measurements to account for rate of change, etc. The memory 87 may be non-volatile such that it retains stored data if the device 80 is powered down. The memory 87 may be, for example, an electrically erasable programmable read-only memory ("EEPROM").

A device 80 of the present invention may comprise a display 88 in communication with the processor 86. The display 88 and processor 86 may communicate by wired and/or wireless communication. The processor 86 may be configured to present the determined remaining capacity by way of the display 88. The remaining capacity may be presented in any suitable form, for example, color-coded (e.g., green-yellow-red), numeric, bar graph, etc. The display 88 may combine multiple forms of presentation. The remaining capacity may be represented as, for example, a percentage value (hereagain, spent or remaining), a time to depletion value, etc. The display 88 may be one or more seven segment displays, LCD screen, LED array, OLED screen, LED screen, or any other visually suitable device, alone or in combination with others.

The processor 86 of the device 80 may be further programmed to control the optical sensors 82 and light sources 84. For example, the processor 86 may be configured to turn on the light sources 84, or each light source 84, only at certain times (e.g., during a sample). Similarly, the optical sensors 82 may be normally off until needed. Such techniques may improve battery life where the device 80 is powered by batteries. The processor 86 may store instructions for these components in a memory 87.

The device 80 may comprise an enclosure 89. The enclosure 89 may be waterproof and/or air tight. Any or all of the other components of the device 80 (e.g., processor 86, light source(s) 84, optical sensor(s) 82, etc.) may be housed within the enclosure 89. At least part of the enclosure 89 may be permeable to light energy. The enclosure 89 may be coated with a material that filters out certain wavelengths of light. The enclosure 89 may be, for example, a translucent plastic formed into a waterproof cylinder. In another embodiment, the enclosure 89 may be a resin or other substance used to coat the other components of the device 80. The enclosure 89 may be configured with a lens to manipulate received or emitted light energy.

Scrubber Description

Scrubbers may be constructed from any material, and have any shape, suitable for a particular application. In some embodiments, multiple scrubbers may be arranged in series, or in parallel, and each scrubber has a flow path in which the substance to be processed moves through the respective scrubber. Generally, a flow path extends from one portion of the scrubber, such as an inlet, and extends to another portion of the scrubber, such as an outlet. The flow path may be linear or non-linear. Depending on the substance to be processed, various sizes, shapes, or distances of the flow path may be beneficial. The inlet and outlet may vary in shape and/or size. The inlet and out may comprise additional components, such as a mesh, grating, etc. The arrangement of optical sensor(s) and light source(s) in a device may be such that the flow path configuration (e.g., shape, size, etc.) is accounted for. For example, the components of the device may be arranged in a generally linear fashion, circular, along multiple axes, etc.

An exemplary scrubber is a cylindrical canister with a single inlet and outlet, where the flow path moves axially through the canister (see, e.g., FIG. 1A). Another example of a scrubber is a cylindrical canister where at least a portion of the radial side of the canister is an inlet and one of the axial ends is an outlet. Still another example of a scrubber is a cylindrical canister with the inlet and the outlet at the same end and wherein one or more baffles direct the flow path through the processing material. Scrubbers may be small in size (e.g., for a single reaction experiment, a single user, etc.) and scrubbers may be large (e.g., for use by multiple individuals, long durations, etc.)

A processing material is disposed along at least a portion of the flow path in the scrubber. The processing material may be a solid, liquid, or gas depending on the requirements of the device. For example, solid granules may be utilized when processing a gas such that the gas comes in contact with the granules in the flow path before exiting an outlet of the scrubber. A common application for such as scrubber is in removing carbon dioxide from a breathing gas, for example, in a breathing (rebreathing) apparatus or in an anesthesia device. In another example, the processing material may be a gas in which a solid material is passed through. Some examples of a processing material include, but are not limited to, soda lime, sodium hydroxide, lithium hydroxide, potassium hydroxide, metal-oxide-based materials, activated carbon, platinum, rhodium, bases, and acids. These processing materials can be configured to vary in an optical characteristic, such as color, according to the remaining capacity of the processing material. This configuration may be inherent to processing material, or added to the processing material through the use of an indicator. One type of indicator may be a pH indicator, such as bromothymol blue.

The processing material may be configured to be replaced, for example, once depleted. In some embodiments, the entire scrubber may be disposable.

Optical Characteristic Detail

The optical characteristic measured by the optical sensors of a device of the present invention may be the color of the processing material (or an indicator in the processing material) or of the substance being processed. The optical characteristic may be a formation or disappearance of a turbidity. For example, if a soluble silver salt is added to a solution of cyanide that contains a trace of iodide, the solution remains clear until all the cyanide has reacted. Upon the addition of more silver, the solution becomes turbid because insoluble silver iodide forms. Iodide is therefore an indicator for excess silver ion in this process. Another kind of optical indicator is an adsorption indicator, such as fluorescein. Fluorescein is used to detect the completion of a process.

The optical characteristic may be measured from light reflected from the measured sample. For example, when measuring the color of soda lime (the processing material), the light source(s) may be configured to illuminate the soda lime and the optical sensor(s) configured to measure the light reflected from the soda lime. The light source may be configured to illuminate an area proximate the optical sensor. In other embodiments, the optical characteristic is measured from light transmitted through the sample. For example, if an optical characteristic of the breathing gas of a rebreather scrubber is to be measured, the optical sensor(s) may be configured to measure unreflected light, transmitted from the light source(s).

In an exemplary embodiment, an infrared $CO_2$ analyzer may be used to measure the optical characteristic. The $CO_2$ analyzer may contain an optical sensor and a light source in the $CO_2$ analyzer package. The $CO_2$ analyzer may provide an indication of the presence of $CO_2$ for the purposes of capacity determination. To detect breakthrough (where the gas is able to pass through the processing material without complete removal of the $CO_2$), the $CO_2$ analyzer may provide quantitative information—i.e., the amount of $CO_2$ present. Such quantitative information may be used to alert the user as the level of $CO_2$ (measured as $PCO_2$—the partial pressure of $CO_2$) approaches a tolerance threshold (beyond which the life of the user will be in jeopardy). For example, the $CO_2$ analyzer may provide percentage $CO_2$ information, which can then be used to derive the partial pressure of $CO_2$. The $CO_2$ analyzer may cooperate with a series of conduits disposed in the flow path. In this way, a single $CO_2$ analyzer may measure an optical characteristic from multiple locations in the scrubber. The conduits may be multiplexed such that the $CO_2$ analyzer is only exposed to one conduit at a time. For example, solenoid valves corresponding to the conduits may be activated in series to multiplex the conduits.

Exemplary Rebreathing Apparatus Embodiment

In an exemplary embodiment of a device for use with a scrubber suitable for a rebreathing apparatus, the scrubber is configured as a cylindrical canister with an axial flow path. The processing material of the scrubber is soda lime with an indicator substance, for example, ethyl violet, which turns violet as the soda lime is consumed. The device of this embodiment comprises a plurality of optical sensors configured to be disposed (when the device is in use) in or near (proximate to) the soda lime along the flow path. The device comprises a light source configured to illuminate at least the portion of soda lime that is proximate to each optical sensor. The optical sensors are configured to measure an optical characteristic of the light reflected from the soda lime. This characteristic may be, for example, the color and/or the luminosity of the reflected light.

The device of this embodiment further comprises a processor in communication with the plurality of optical sensors and programmed to determine a remaining capacity of the scrubber based on the light values reflected by the processing material. The processor may determine the remaining processing capacity based on the light value measured by the optical sensor.

Embodiments of devices according to the present invention may comprise a final light source and final optical sensor. The final light source and final optical sensor may be located near an outlet of a scrubber. These components may act as a safety check that can alert a user if the processing material has depleted its capacity sooner than expected, or if there is a failure in the scrubber or processing material.

Method Embodiments

The present invention may also be embodied as a method 100 for determining a remaining processing capacity of a scrubber. The scrubber has a flow-path and a processing material disposed along at least a portion of the flow path. As described above, the processing material may be configured to vary in an optical characteristic, such as color, according to the remaining capacity of the processing material.

The method 100 comprises the step of providing 101 a device, which may be similar to the device described above. The provided 101 device may have a plurality of optical sensors disposed within the processing material and arranged along the flow path of the scrubber. The device may also have a light source and a processor.

The method 100 comprises illuminating 103 the processing material with the light source. The light source may illuminate 103 the processing material adjacent to each optical sensor. The illumination 103 may vary in duration. For example, long duration illumination 103 may be used to collect additional data, and short duration illumination 103 may be used to conserve energy and prolong battery life. If multiple light sources are provided, each light source may illuminate 103 sequentially or simultaneously.

The method 100 comprises measuring 105 a light value using the optical sensor. The optical sensor may measure 105 a light value reflected by the processing material. Where there are multiple optical sensors, the sensors may measure 105 a light value simultaneously or sequentially. During measuring 105, the optical sensors may convert received light into an electric signal (digital or analog). The measured 105 light value may be any characteristic of light including, but not limited to, phase, luminosity, luminance, and wavelength. Measuring 105 the light values may be performed by each optical sensor sequentially. The device may be configured to illuminate the processing material at intervals in order to reduce power consumption. For example, the light sources may be illuminated one at a time in a sequential fashion. There may be a time delay between light source illumination depending on the requirements of the device.

The method 100 comprises determining 107 the remaining processing capacity of the scrubber using the processor, based on the measured 105 light value. The processor may be programmed to determine 107 an estimated remaining time before exhaustion of the processing material based on the remaining processing capacity and the rate of change of the processing capacity. Because the optical sensors are placed along the flow path, the processor may determine how quickly the processing material is being depleted. For example, if five sensors are placed in the flow path, the processor can determine 107 a processing capacity percentage based on the summation of the sensor measurements. The processor may determine 107 a remaining processing capacity by tracking the measured 105 light value over time. In another embodiment, the processor may determine a rate of processing capacity consumption.

The method 100 may comprise the step of storing 109 the measured 105 light value from each optical sensor in a memory. The memory may be a component of the provided device. The memory may be non-volatile such that the contents of the memory persist after the device is powered down. Multiple measured 105 light values may be stored in the memory. Other information may also be stored in the memory, such as rate of processing material consumption, remaining processing material capacity, and a time corresponding to stored information.

The steps of illuminating 103 the processing material, measuring 105 the light value at each optical sensor, and storing 109 the measured 105 light values may be repeated at least once. The steps may be repeated programmatically, or on the user's demand. The rate of repetition maybe controlled by the processor. The rate of repetition may be static or dynamic. The stored 109 data may be used to more accurately determine 107 the remaining capacity by, for example, accounting for the rate of change of measured 105 light. The method 100 may comprise the step of storing 111 the determined 107 remaining processing capacity. In this way, previous determinations of remaining capacity may further inform the present determination 107.

The method 100 may further comprise the step of displaying 113 the determined 107 remaining capacity on a display. Other information may be displayed on the display, such as rate of processing material consumption, time before processing material depletion, and historical information.

Another embodiment of the present invention can be described as a method for determining a remaining processing capacity of a processing container. The processing container has a flow path and a processing material disposed along at least a portion of the flow path. The method may comprise the steps of providing a device, emitting light energy, measuring a light value, and determining the remaining processing capacity based on the measured light value. The provided device may be similar to any of the devices listed above, and comprises an optical sensor, a light source, and a processor. The optical sensor may be disposed in a portion of the flow path of the processing container. The light source may be configured to emit light energy in an area at least partially adjacent to the optical sensor.

Further Exemplary Embodiment

Figure 2:
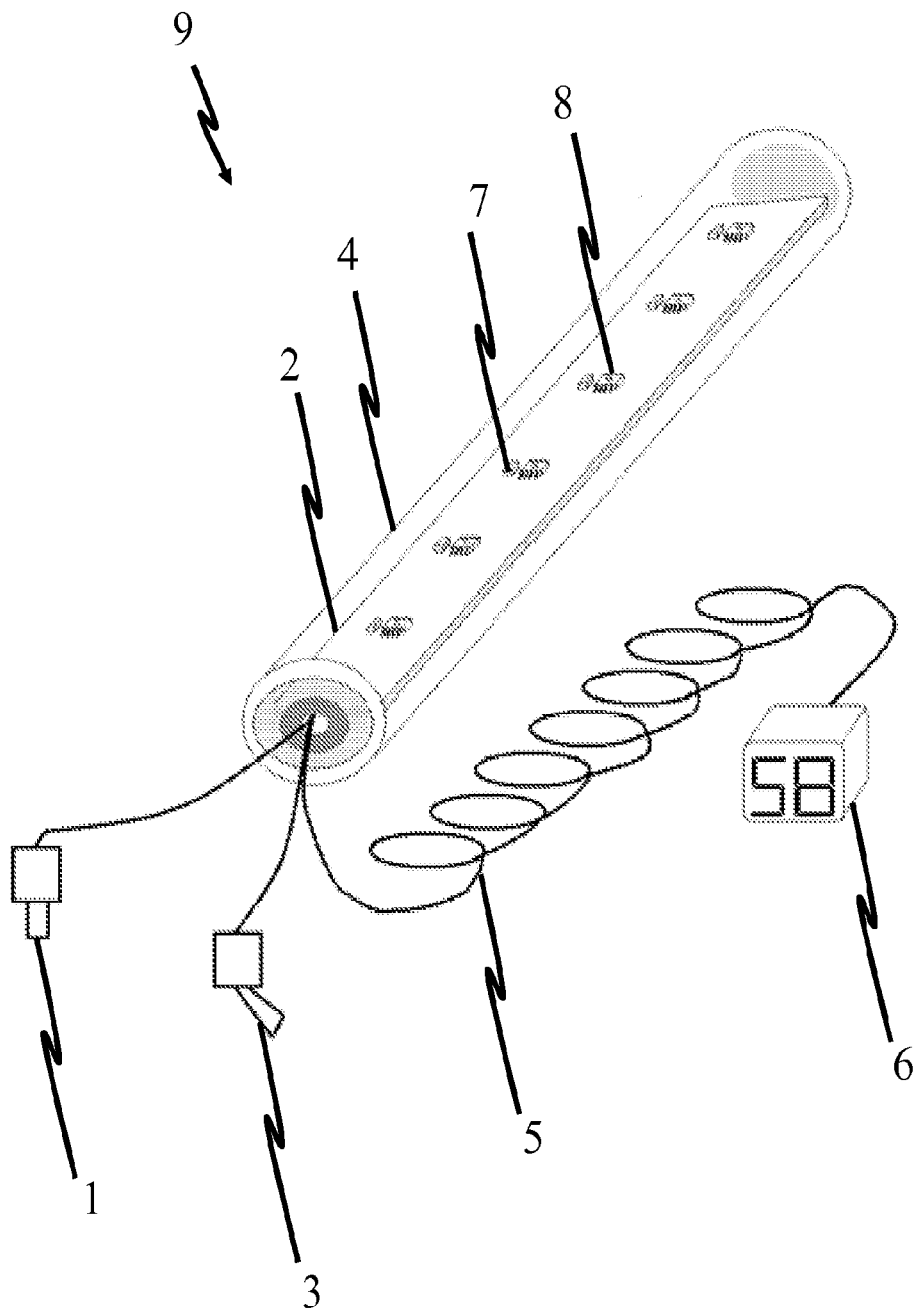
FIG. 2 depicts a device according to another embodiment of the present invention.

The invention may be embodied as a device 9 (see, e.g., FIG. 2). The device 9 may comprise a waterproof clear cylinder 4 enclosing a printed circuit board 2. The printed circuit board 2 is configured to accept light source 7 and optical sensor 8. The device 9 may also comprise a fresh soda lime switch 1, an on/off switch 3, and a display 6. The display 6 may be connected to the printed circuit board 2 and the remainder of device 9 through set-up wires 5.

The device 9 is configured to emit light from light source 7 which reflects off a processing material. The optical sensor 8 measures the reflected light as a light value. The light values measured by each optical sensors 8 are communicated to a microprocessor (not shown in this figure) and the microprocessor determines a remaining capacity of the scrubber. As the processing material's capacity is depleted, the optical sensors 8 measure light values and the microprocessor determines capacity according to the new values accordingly.

Figure 3:
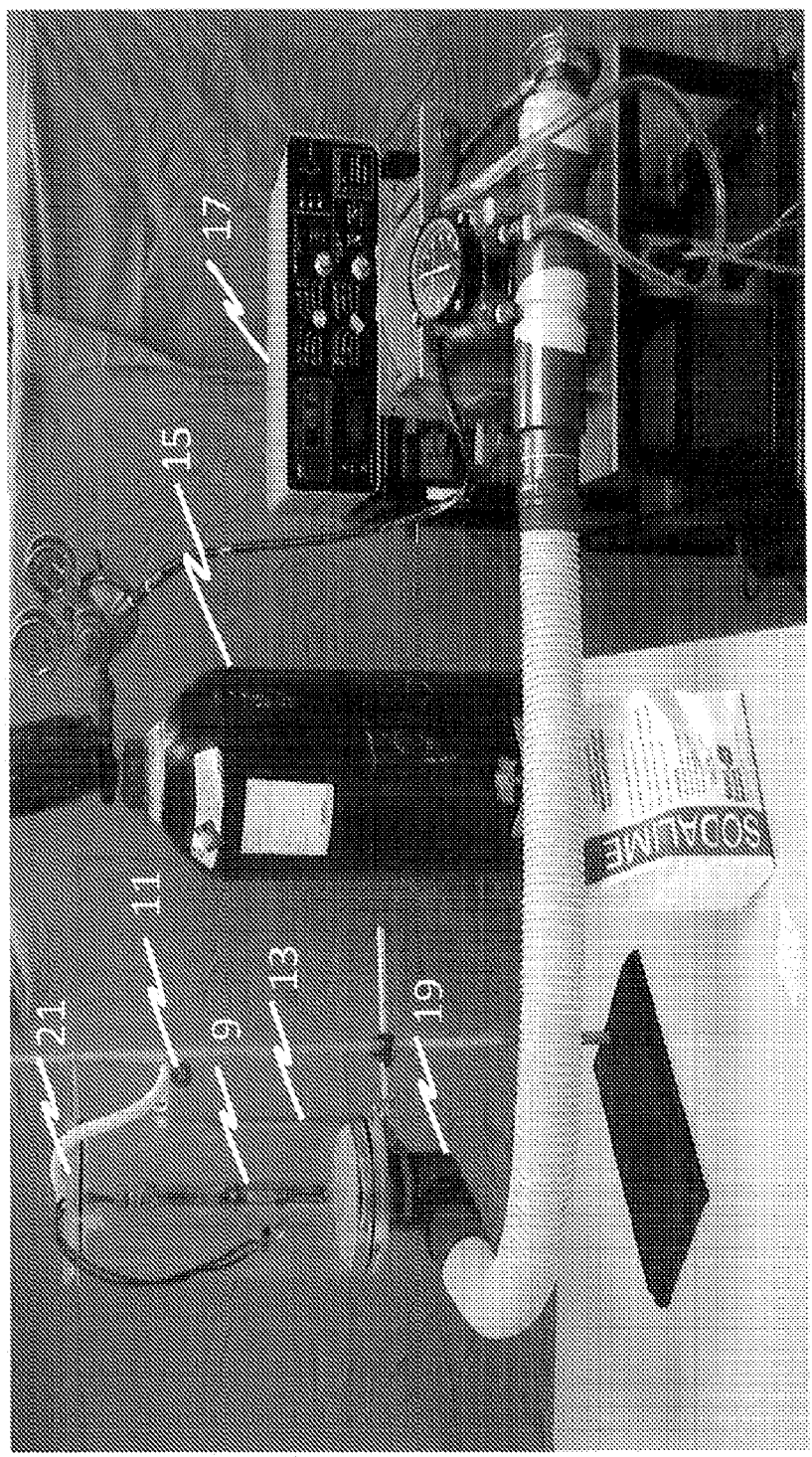
FIG. 3 illustrate an apparatus used to test a device of the present invention.

FIG. 3 illustrates an apparatus used to test the exemplary device 9. The device 9 is placed in a scrubber 13. The scrubber 13 is filled with a processing material (not shown). The scrubber contains an inlet 19 and an outlet 21. Gas moves through the scrubber 13 in a flow path from the inlet 19 to the outlet 21. The gas may also move through the scrubber 13 and into a rubber or plastic bag (not shown). This is often called a re-breathing bag. The re-breathing bag can be placed upstream or downstream of the scrubber 13.

In a test configuration, the gas comprises air mixed with $CO_2$ from tank 15. Control pump 17 mixes the $CO_2$ with ambient air and moves the gas through the scrubber 13 in such a way that mimics human respiration. As such, the control pump 17 may be programmed to deliver respiration of various intensities and speed. For example, a breathing gas mixture containing 5% $CO_2$ in air can be driven by the control pump 17 through the scrubber 13 at rates and volumes which simulate breathing. A display 11 is used to communicate information to the operator.

An example of a processing material is non-hygroscopic soda lime. The soda lime may be mixed with an indicator that changes color to indicate the remaining absorptive capacity of the soda lime. Soda lime is typically used to remove exhaled $CO_2$ in a closed circuit (re-breather type) breathing apparatus because re-inhaling exhaled gas containing $CO_2$ is hazardous to the diver. A suitable soda lime for use with the embodiments of the present invention are commercially available as SOFNOLIME® by Molecular Products Limited, Mill End, Thaxted, Essex, CM6 2LT, United Kingdom. In some embodiments it may be desired to use a $CO_2$ absorbent material that contains a dye additive which changes color from white to violet as its $CO_2$ absorption capability diminishes with usage, i.e., as the level of absorbed $CO_2$ rises.

Figure 4:
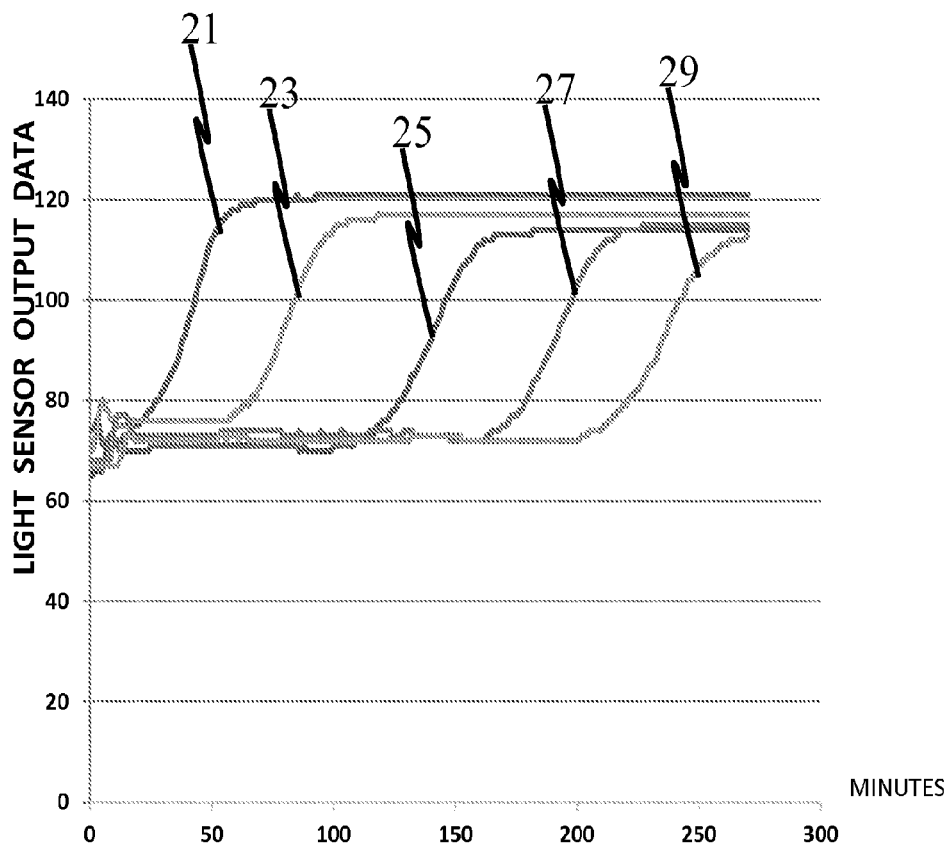
FIG. 4 is a graph showing light values measured over time by the optical sensors of a device according to an embodiment of the present invention.

When the scrubber 13 of FIG. 3 is filled with a processing material, and the device 9 is activated in conjunction with the control pump 17, the test apparatus simulates a typical re-breathing apparatus used by divers, firefighters, persons who must function in other noxious environments, etc. FIG. 4 illustrates the optical sensor 8 output data of a device which was constructed with five optical sensors 8 arranged at various positions in the scrubber 13 flow path. As time progresses, each optical sensor 8 outputs a signal which changes according to the measurement and correlated with the respective optical sensor's 8 placement in the flow path. In this example, the first optical sensor 8 is located closest to the inlet 19. As the processing material becomes spent and changes its optical characteristics, the first optical sensor's measured light value 21 indicates the change of capacity by increasing according to the change in the optical characteristic being measured. Likewise, measured light values 23, 25, and 27 of subsequent optical sensors 8 indicate the change of the processing material's optical characteristics as the processing material is gradually spent. Light value 29 represents a final optical sensor 8 near the outlet 21 of the scrubber 13. By combining the measured light values 21, 23, 25, 27, and 29 from all of the optical sensors 8, the remaining processing capacity of the processing material can be determined accurately.

For example, the remaining processing capacity may take into account factors such as: (1) how much of the processing capacity has already been used, and (2) the ongoing loading being presented to the processing material. With reference to a re-breather, the device 9 can take into account the current $CO_2$ scrubbing capacity of the absorbent material, and the current loading rate at which the absorbent material is being used. This loading depends on the current rate of $CO_2$ generation, i.e., the physical activity of the diver. Devices according to embodiments of the present invention also advantageously account for, and/or are insensitive to, other externalities, such as, the quality of the soda lime, the temperature of the operating environment, etc. Thus, he/she can modify their own physical activity in order to make the best use of the remaining processing material capacity. As safety may dictate, he or she may wish to allow more time for a safe return to the surface.

Figure 5:
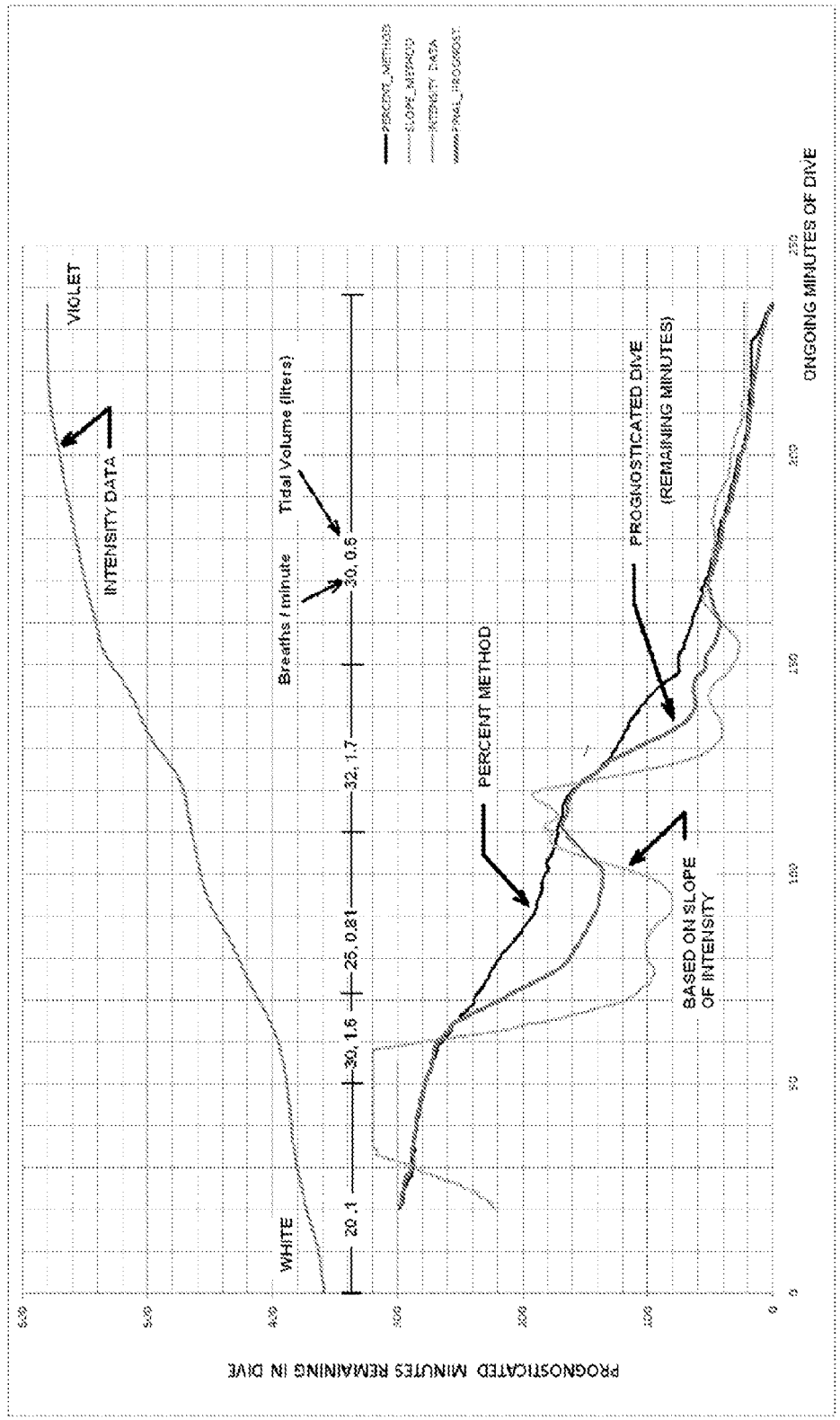
FIG. 5 is a graph showing the determined remaining capacity, calculated by more than one technique, during an exemplary use of a device according to the present invention.

FIG. 5 illustrates a simulated diving scenario using device 9. In this scenario, the breaths per minute and tidal volume of the simulated diver change over time. These changes simulate changes in diver exertion and activity. The upper portion of FIG. 5 shows a summed intensity value 21, 23, 25, 27, and 29 (the "total intensity" or "intensity data") measured by the optical sensors 8. The slope of the intensity data utilized to determine the rate of consumption of the processing material. For example, the slope of the intensity data is greatest when the simulated diver is breathing 32 times per minute at a tidal volume of 1.7 liters, and the slope is the least when the simulated diver is breathing at a lower rate, for example, 20 times a minute at a tidal volume of 1.0 liter. The remaining capacity of the processing material can be determined through a percentage method, the slope of intensity, or a combination of the two. The combination allows the diver to receive immediate feedback about his/her exertion and adjust his/her diving plan accordingly. For example, at minute 80, the diver could assess whether or not to continue at the current level of exertion (resulting in a reduced dive time) or reduce exertion in order to increase the total dive time.

Figure 6:
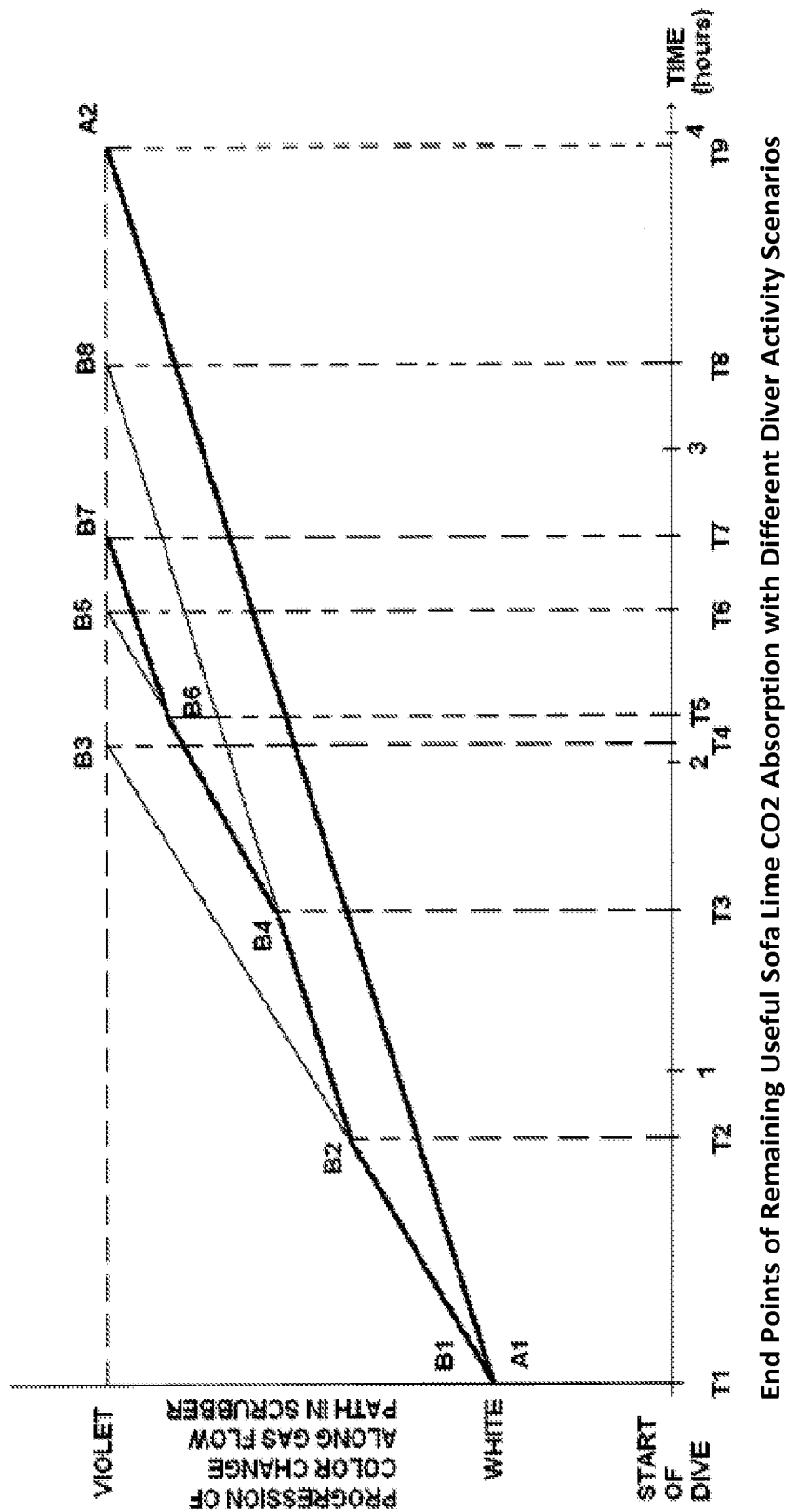
FIG. 6 is a graph showing various end points of useful soda lime corresponding to different diver activity scenarios.

FIG. 6 shows, in a dimensionless fashion on the vertical axis, progress from white (highly reflective color of unused soda lime) to dark (poorly reflective violet color of spent soda lime) against time on the horizontal axis. The line drawn from point A1 to point A2 represents a hypothetical dive in which a healthy human is at rest throughout the entire dive. Time T1 is the start of the dive, and T9 would be the predicted duration of the soda lime (slightly less than 4 hours). This predicted duration number in FIG. 6 is arbitrarily chosen. The actual predicted duration number would vary with the size of the scrubber and the total amount of soda lime. In FIG. 6, the B line represents a more realistic scenario in which the swimmer's activity level, and consequently his/her rate of $CO_2$ production, changes several times during the dive.

For example, the dive begins at time T1. From B1 to B2 the diver is swimming at a steady pace. The B2-B3 line is the predicted soda lime duration time of T4 (2 hours and 4 minutes), assuming that the diver's activity level remains constant. This may not be the number which is displayed on the diver's facemask display. The microcontroller can continuously subtract the amount of time which has expired from the predicted total usage time, and the difference is the value which will be displayed. As the dive continues from T2 to T3 we now see that the diver's activity level, and consequently rate of $CO_2$ production, has declined. If he/she were to continue at this new rate the predicted service time of the soda lime would be to point B8. This corresponds to T8 on the x-axis (3 hours and 17 minutes). The time displayed on the facemask display would be this number minus the time already spent. As the dive continues from T3 to T5 the diver's activity level has increased. B5 is the predicted point for the end of soda lime useful life. At point B6 the activity level is reduced again and remains there until dive completion at B7. This corresponds to T7 on the x-axis (2 hours and 45 minutes). The time displayed on the facemask display would be this number minus the time already used. In this case the time in use would be greater than the value predicted at T5.

In some situations, a processing material with an indicator may experience what is known as blanching. For example, the soda lime color change from white to violet (or other dark color) is a temporary event, and the soda lime will change back to white if it is not subject to $CO_2$ loading (i.e. if the diver is not breathing on the gear). The present invention solves this problem through the use of non-volatile memory. The last known processing capacity of the processing material may be stored in the device's memory. For example, if a soda lime charge in the canister is used more than once, the microcontroller will remember how much absorption time was available at the end of use. This end value will be the starting value for subsequent use. Accordingly, the device has a component for notifying the processor when fresh soda lime has been loaded, for example, a switch for the user's input, or an interconnect on a cover of the scrubber.

Figure 7:
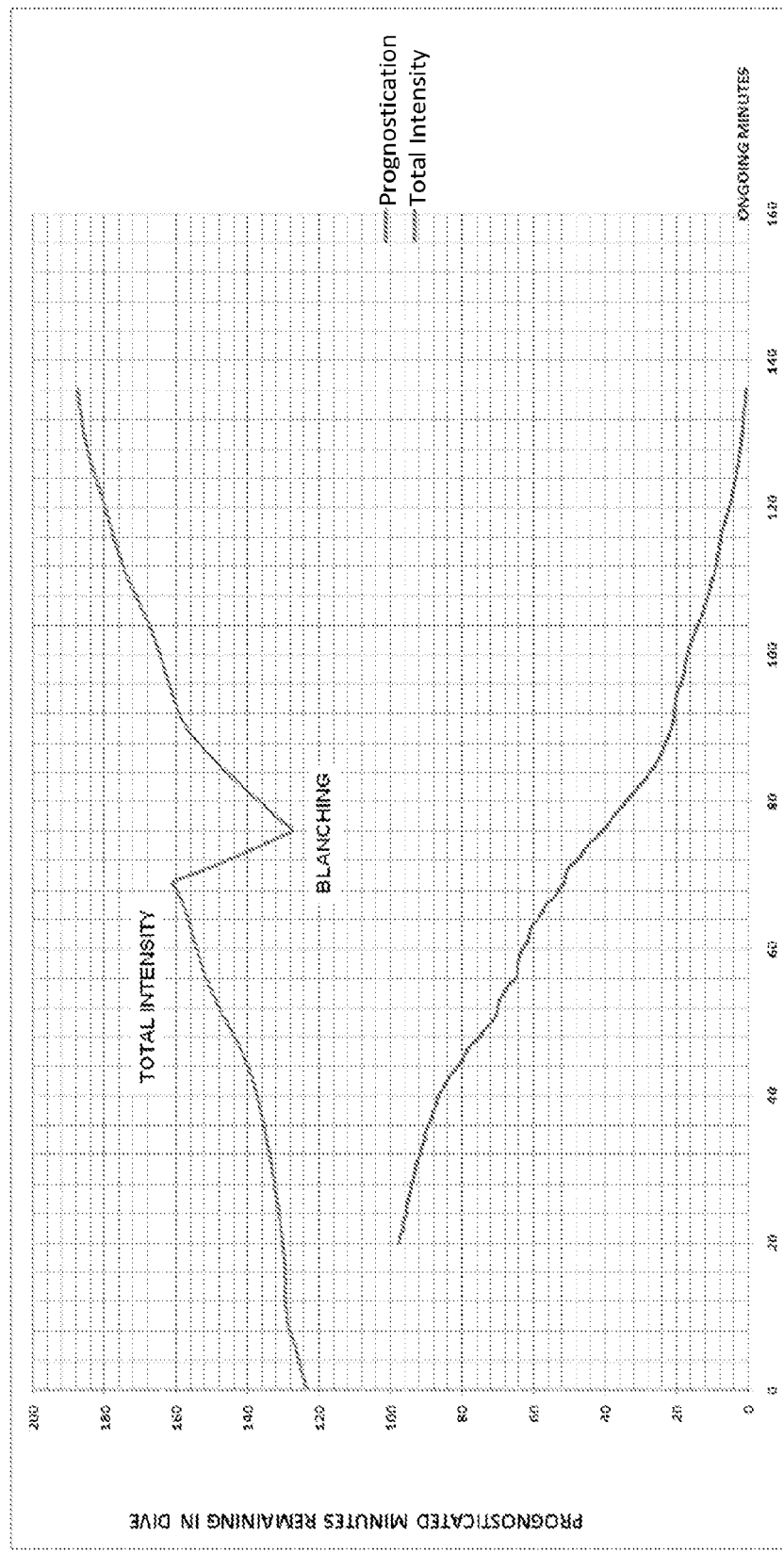
FIG. 7 is a graph showing the determined remaining capacity of a device according to the present invention, showing the effect of blanching due to a period of non-use.

FIG. 7 illustrates the prognosticated time remaining in a dive when the processing material experiences the blanching effect. At approximately 70 minutes, the first portion of a simulated dive is completed (i.e., the diver surfaces and stops using the re-breather). The processing material is allowed to rest for an extended length of time; however, the last known processing material capacity is stored in the device's non-volatile memory. This stored value has been calculated based on the intensity of $CO_2$ production, i.e., the diver's physical activity deduced from the rate of advancement of the color change of the soda lime during the earlier dive. Any higher diver activity in a subsequent dive will cause the prognosticated use time to be reduced; a lower activity level will cause the display to indicate a longer remaining use time and slower decline thereof. When the second portion of the dive commences, the intensity data obtained from the optical sensors indicates that the soda lime has blanched back to an apparently unused condition. Since the last prognosticated time and remaining capacity values were previously stored in the device, and the device knows that fresh soda lime has not been loaded (i.e., the fresh soda lime switch has not changed state) it will assume that a power down/power up sequence occurred. The device will then display the last known prognostication values which were stored in its nonvolatile memory before the power down occurred.

The processor will continue to monitor the optical sensor outputs. It is known that once $CO_2$ begins to flow again, the used soda lime will quickly return to its formerly violet state. Once the optical sensors indicate that the soda lime has returned to the levels seen in the earlier usage, normal calculations of remaining capacity and remaining usage time will resume.

If the processor ever detects a color change in the processing material which occurs too rapidly, the processor could be programmed to issue a warning to the user that he/she is breathing through previously exhausted (and thus ineffective) soda lime.

For example, if a charge of fresh soda lime is placed in the scrubber canister, the rate of $CO_2$ production may be set to 0.3 L/min at the start of the dive. This is the typical rate of $CO_2$ production of a resting adult. If soda lime, which was partly saturated with $CO_2$ in an earlier dive, is to be used then the remaining use time after the earlier dive becomes the starting point for this subsequent dive. As soon as the new dive has started the system will monitor the rate of progression of the color change in the scrubber and prognosticate the available remaining use time. The microcontroller will sample the color change data frequently in order to allow for changes in diver activity. For example, sampling all sensors once per minute would be typical. At any time during the dive, updated prognosis of remaining $CO_2$ absorption time may be displayed in hours and minutes on a small facemask-mounted display.

Figure 8:
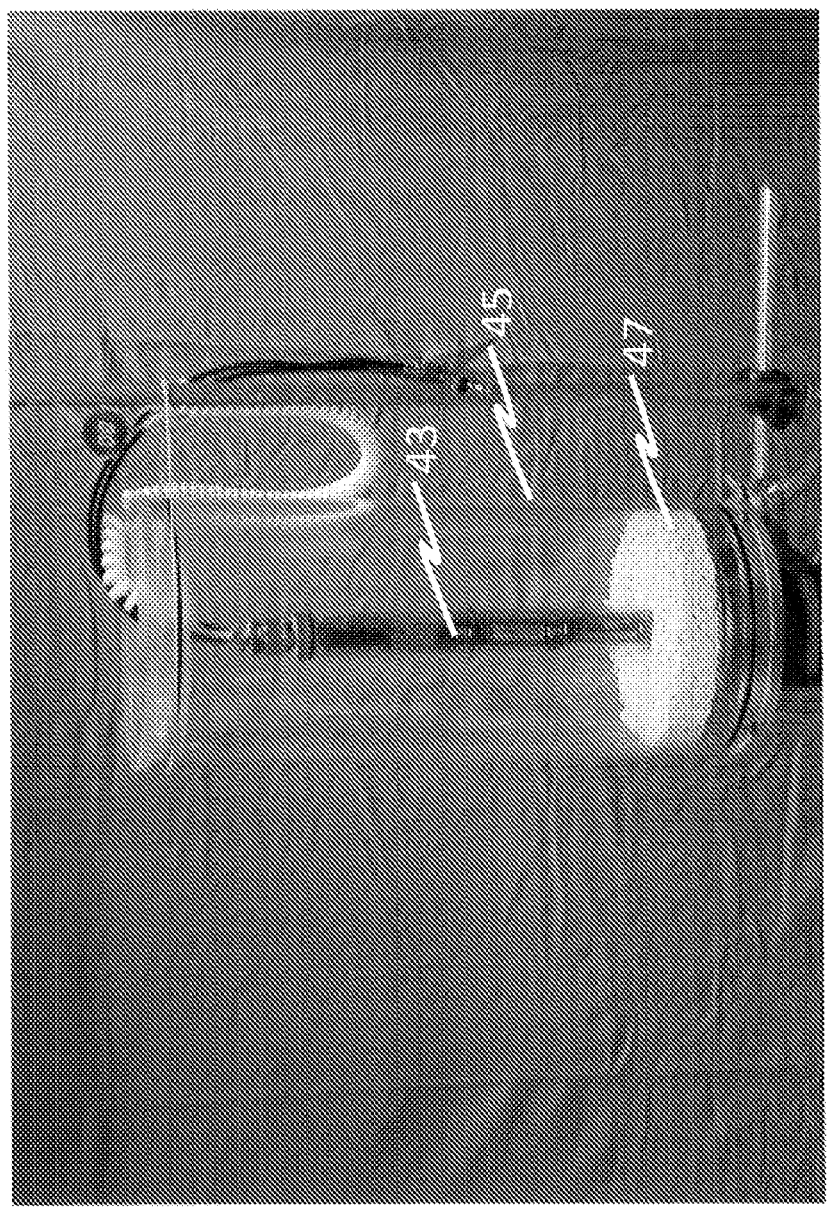
FIG. 8 is an illustration of a scrubber having a device according to the present invention disposed along a portion of the flow path.

FIG. 8 shows a scrubber 45 partially loaded with processing material 47. In use, the processing material 47 would likely cover the entirety of device 43. In this embodiment, display 41 uses two seven segment displays to communicate processing capacity data to the user.

Figure 9:
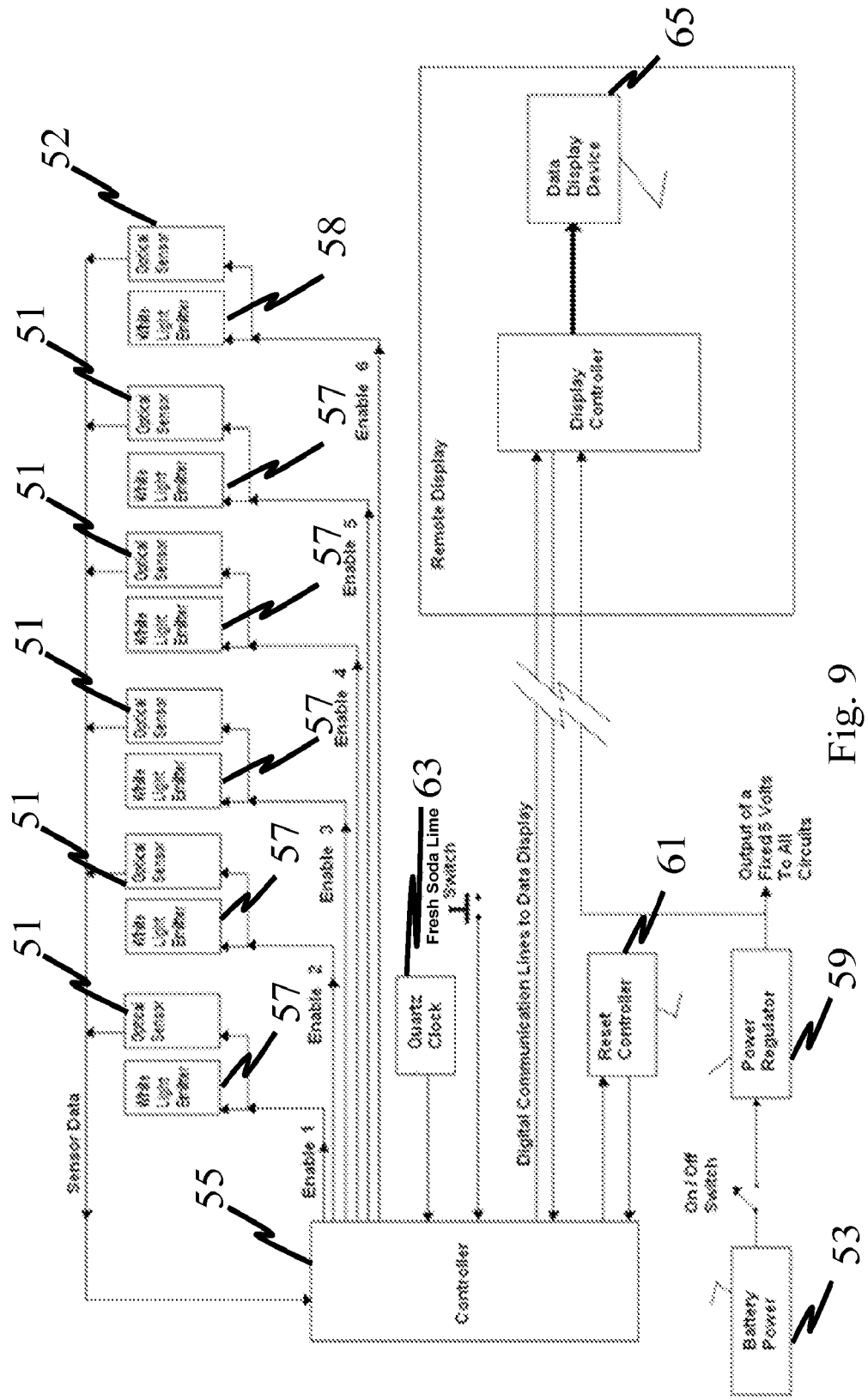
FIG. 9 is a block diagram of a device according to an embodiment of the present invention.
Figure 10:
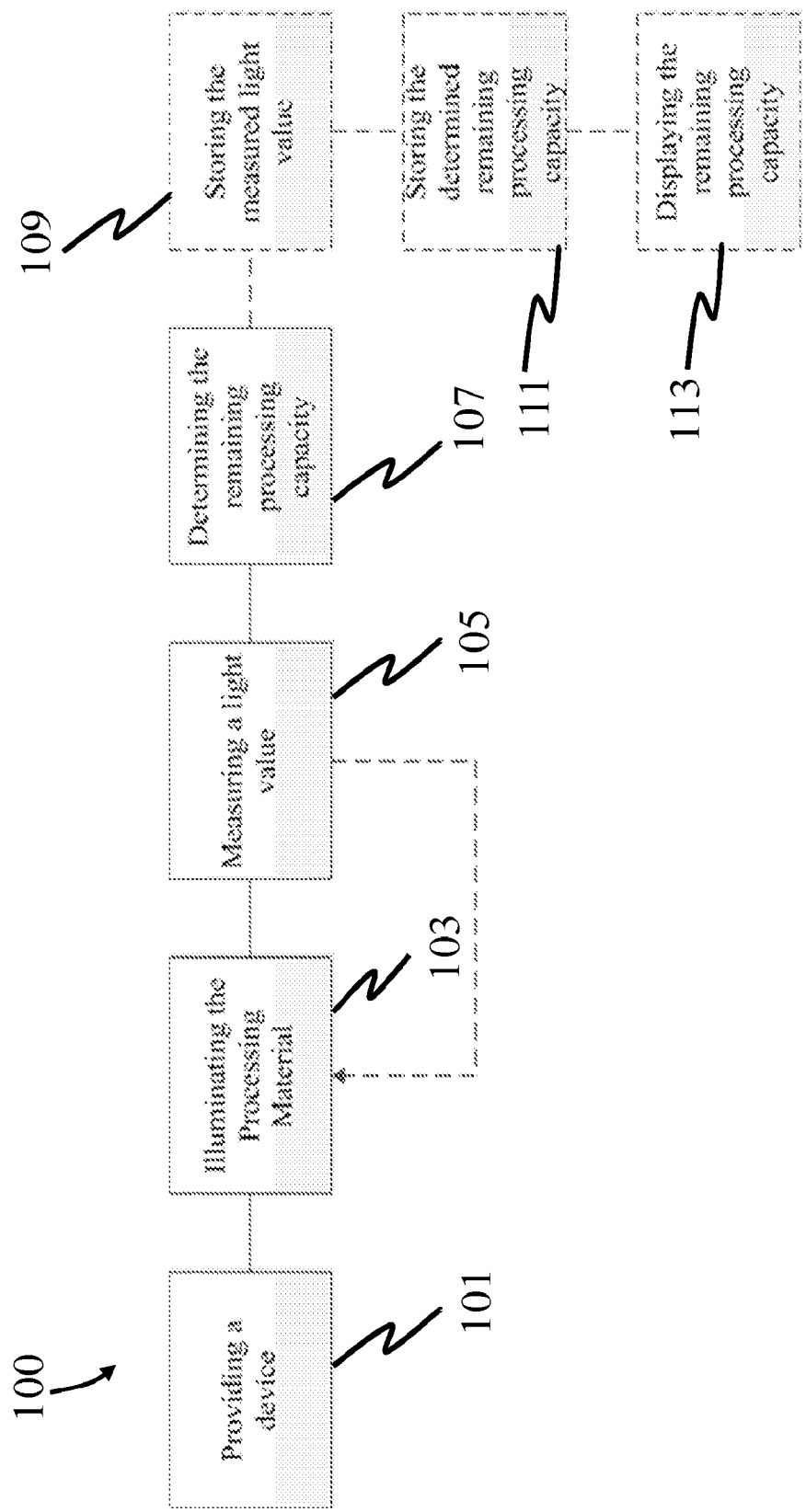
FIG. 10 is a flowchart depicting a method according to an embodiment of the present invention.

FIG. 9 shows a block diagram of an embodiment of a device according to the present invention. A device implementing the diagram illustrated in FIG. 9 can be placed in a $CO_2$ scrubber canister. Multiple types of scrubbers exist, including, for example, an axial scrubber. The present invention can be configured to work in different types of scrubbers. In some embodiments, the device is powered by two AAA batteries 53 which can provide at least 30 hours of use. There are six optical sensor integrated circuits shown 51, 52. Five of the optical sensor circuits monitor the change in light intensity that is reflected off the soda lime pellets. As the soda lime changes from white to violet (or any other darker than white color) the intensity of the reflected light will diminish. This change will be read by the microcontroller 55. An example of a suitable optical sensor is the TSL230ARD by TAOS. Five light sources 57 illuminate the soda lime one at a time until its corresponding light sensor integrated circuit obtains a reading of light intensity. In some embodiments, the light sources 57 may emit light simultaneously. The sixth optical sensor 52 is a dedicated safety check and will be mounted near to where the exhaled gas exits the $CO_2$ scrubber. Its corresponding LED 58 will illuminate a small quantity of soda lime which is used to detect any breakthrough of $CO_2$. Normally, no $CO_2$ should be present near optical sensor 52 because the $CO_2$ should be absorbed by the scrubber's soda lime before reaching optical sensor 52. If a change is detected by optical sensor 52, the microcontroller 55 can immediately display a 'no time left' warning on a display, such as flashing the word "no."

In some embodiments, a switching voltage regulator 59 steps up the battery voltage, which can vary from 2.5 to 3.2 volts, to a fixed, well-regulated 5 volts. A watchdog timer circuit 61 may control the microcontroller's RESET input. As long as the firmware is running correctly the microcontroller 55 can periodically pulse watchdog timer circuit 61. If the pulsing should cease, the watchdog timer 61 would reset the microcontroller 55 and this would force the firmware to start over, or reboot. The device may utilize an on-off switch to shut down the device when not in use to conserve battery life.

A quartz crystal 63 may be provided which oscillates at a fixed rate. For example, the quartz crystal 63 may oscillate at a 20 megahertz rate. The quartz crystal 63 may be used as the system clock which steps the microcontroller 55 through each of its internal instructions. It also enables the accurate measurement of time as the soda-lime gradually changes color with use.

When the scrubber's processing material is replaced, the microcontroller 55 can be configured to perform a self-calibration of the observed white color and store new constants for the sensor outputs in its permanent memory (not shown). One example of this permanent memory may be an EEPROM device.

The device may also have a "fresh soda lime" switch to signal the microcontroller that the scrubber has been charged with fresh processing material. The fresh soda lime switch signals the microcontroller to reset (zero out) any previously stored data and prevent it from falsely concluding that use has resumed which will utilize old processing material. The fresh soda lime switch could be a mechanical interlock of some sort which automatically changes state when the old processing material is removed and new processing material is put in.

The device may also include a display 65. For example a junction point may be used to connect the $CO_2$ scrubber to a facemask mounted LED display. Wires may be used to transmit and receive serial data. The display can be a facemask mounted LED display which informs a diver how much dive time is left in hours and minutes. Other types of displays could also be used. For example backlit LCD (liquid crystal display), or OLED (Organic light emitting diode) display may be suitable.

The display 65 may also be used to communicate other information to a user. The display 65 may have a microcontroller, but the microcontroller may have less capability than the microcontroller 55 of FIG. 9. The display 65 microcontroller can receive serial data from the scrubber unit and display it on a seven segment display. For example, the data may be transmitted at 9600 baud. The display 65 microcontroller may turn on only one segment of the seven segment display at a time. The segments can be multiplexed very quickly (400 microseconds for each segment) in order to keep power consumption at a minimum. The human eye cannot detect the high speed multiplexing, the user will observe multiple segments simultaneously. This seven segment display may indicate if the battery 53 is low. For example, the display may read "bA" during a low battery condition. Normally, the seven segment splay may indicate "xh," delay for 1 second, and then display "yy." The "h" is used to indicate the number of remaining useful hours. The "x" is the number of hours and "yy" is the number of minutes remaining. The display may also be configured to provide an exertion meter or rate-of-use meter to the user, such that the user can adjust his/her actions, or the inputs of the system to manage the rate of processing material consumption.

In an exemplary embodiment of a method according to the invention, a controller functions as the central processing unit for all of the processing capacity device's operations. The controller contains an internal program code sequence which instructs it to do the following: (a) activate a light source (e.g., an LED) and read a reflected optical light characteristic from an optical sensor; (b) repeat this operation for the plurality of light sources and optical sensors; (c) process the sensor information and prognosticate remaining processing capacity; (d) convert this information to hours and minutes and then transmit it to a display; and (e) store, in its own nonvolatile (permanent) memory, all the relevant processing material usage information.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A device for determining a remaining processing capacity of a scrubber having a flow path and a processing material disposed along at least a portion of the flow path, the processing material configured to vary in color according to the remaining capacity of the processing material, the device comprising:
    a plurality of optical sensors for measuring reflected light values from the processing material, the plurality of optical sensors configured to be disposed proximate the processing material and arranged along at least a portion of the flow path;
    a light source configured to illuminate the processing material proximate the plurality of optical sensors; and
    a processor in communication with the plurality of optical sensors, wherein the processor is programmed to determine a remaining processing capacity of the scrubber based on the light values reflected by the processing material measured by each optical sensor of the plurality of optical sensors.

2. The device of claim 1, further comprising a memory in electrical communication with the processor and configured to store the reflected light values.

3. The device of claim 2, wherein the memory is nonvolatile.

4. The device of claim 1, wherein the processor is programmed to determine an estimated remaining time based on the remaining processing capacity and the rate of change of the processing capacity.

5. The device of claim 1, further comprising a display in communication with the processor for displaying a determined remaining processing capacity.

6. The device of claim 1, wherein the processor is programmed to determine a rate of processing capacity consumption.

7. The device of claim 1, wherein the light source comprises a plurality of light sources, and each light source of the plurality of light sources corresponds to an optical sensor of the plurality of optical sensors.

8. The device of claim 7, wherein a final light source and a final optical sensor are located near an exit of the scrubber with respect to the flow path.

9. A device for determining a remaining processing capacity of a processing container having a flow path and a processing material disposed along at least a portion of the flow path, the device comprising:
    an optical sensor for measuring light values, the optical sensor configured to be disposed in a portion of the flow path;
    a light source configured to illuminate an area proximate the optical sensor; and
    a processor in communication with the optical sensor, wherein the processor is programmed to determine a remaining processing capacity of the processing container based on the light value measured by the optical sensor.

10. The device of claim 9, wherein the optical sensor and the light source are contained within a $CO_2$ analyzer.

* * * * *